United States Patent
Breyne et al.

(10) Patent No.: US 6,426,023 B1
(45) Date of Patent: Jul. 30, 2002

(54) BENZOPYRANS ANNELATED IN $C_7$-$C_8$ WITH AN AROMATIC HETEROCYCLE AND COMPOSITIONS AND (CO)POLYMER MATRICES CONTAINING THEM

(75) Inventors: Olivier Breyne; You-Ping Chan; Patrick Jean, all of Lyons (FR)

(73) Assignee: Corning, S.A., Avon Cedex (FR)

( * ) Notice: Subject to any disclaimer, the term of this patent is extended or adjusted under 35 U.S.C. 154(b) by 0 days.

(21) Appl. No.: 09/590,000

(22) Filed: Jun. 8, 2000

(30) Foreign Application Priority Data

Jun. 10, 1999 (FR) .............................. 99 07355

(51) Int. Cl.[7] .................. G02B 5/23; C07D 311/78; G02C 7/10
(52) U.S. Cl. ............... 252/586; 351/163; 548/417; 548/418; 549/41; 549/381; 549/382
(58) Field of Search .................. 252/586; 351/163; 548/417, 418; 549/41, 381, 382

(56) References Cited

U.S. PATENT DOCUMENTS

| | | |
|---|---|---|
| 5,514,817 A | 5/1996 | Knowles |
| 5,565,147 A | 10/1996 | Knowles et al. |
| 5,645,767 A | 7/1997 | Van Gernert |
| 5,783,116 A | 7/1998 | Lin |
| 5,869,658 A | 2/1999 | Lin |
| 5,955,520 A | 9/1999 | Heller et al. |
| 5,961,892 A | 10/1999 | Gemert et al. |
| 6,022,495 A | 2/2000 | Kumar |
| 6,022,497 A | 2/2000 | Kumar |

FOREIGN PATENT DOCUMENTS

| | | |
|---|---|---|
| DE | 197 41 705 A1 | 9/1997 |
| EP | 0 562 915 | 9/1993 |
| WO | 94/22850 | 10/1994 |
| WO | 95/05382 | 2/1995 |
| WO | 95/27716 | 10/1995 |
| WO | 97/48762 | 12/1997 |
| WO | 99/15518 | 4/1999 |

*Primary Examiner*—Philip Tucker
(74) *Attorney, Agent, or Firm*—Angela N. Nwaneri; Peter Rogalskyj

(57) ABSTRACT

The invention relates to novel benzopyran-type compounds having an aromatic heterocycle annelated in position 7,8 and a carbocycle annelated in position 5,6. These compounds have the formula (I) given below:

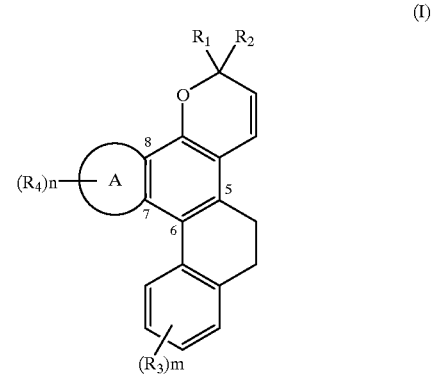

These compounds (I) have interesting photochromic properties. The invention also relates to their preparation, to their applications as photochromes, as well as to the compositions and (co)polymer matrices containing them.

18 Claims, No Drawings

BENZOPYRANS ANNELATED IN $C_7$-$C_8$ WITH AN AROMATIC HETEROCYCLE AND COMPOSITIONS AND (CO)POLYMER MATRICES CONTAINING THEM

CROSS REFERENCE TO RELATED APPLICATIONS

This application claims the benefit of French Patent Application No. 99 07355, filed Jun. 10, 1999, entitled Benzopyrans Annelated In $C_7$-$C_8$ With An Aromatic Heterocycle And Compositions And (Co)Polymer Matrices Containing Them, by Olivier Breyne, You-Ping Chan and Patrick Jean.

The present invention relates to novel benzopyran-type compounds which are annelated in $C_5$-$C_6$ and $C_7$-$C_8$ and which have, in particular, photochromic properties. The invention also relates to photochromic compositions and photochromic ophthalmic articles (lenses for example) which contain said benzopyrans. The invention also covers the preparation of these novel compounds.

The photochromic compounds are capable of changing colour under the influence of a poly- or mono-chromatic light (UV for example) and of returning to their initial colour when the luminous irradiation ceases, or under the influence of temperature and/or a poly- or mono-chromatic light different from the first.

The photochromic compounds find applications in various fields, e.g. for the manufacture of ophthalmic lenses, contact lenses, solar protection glasses, filters, camera optics or photographic apparatus optics or other optical devices and observation devices, glazing, decorative objects, bill elements or even for information storage by optical inscription (coding).

In the field of ophthalmic optics, and in particular the spectacles trade, a photochromic lens which comprises one or more photochromic compounds must have:

- a high transmission in the absence of ultraviolets,
- a low transmission (high colourability) under solar irradiation,
- adapted coloration and discoloration kinetics,
- a tint acceptable to the consumer (grey or brown preferably) with preferably a maintenance of the chosen tint during the coloration and the discoloration of the lens,
- a maintenance of the performances, the properties, within a temperature range of 0–40° C.,
- a significant durability, since these objectives sought after are sophisticated corrective lenses and therefore expensive.

These lens characteristics are in fact determined by the active photochromic compounds which they contain; compounds which must furthermore be perfectly compatible with the organic or inorganic support which constitutes the lens.

Moreover, it is to be noted that obtaining a grey or brown tint may necessitate the use of at least two photochromes of different colours, i. e. having distinct maximal absorption wavelengths in the visible. This combination further imposes other requirements of the photochromic compounds. In particular, the coloration and discoloration kinetics of the (two or more) combined active photochromic compounds must be essentially identical. The same applies for their stability with time and also for their compatibility with a plastic or inorganic support.

Amongst the numerous photochromic compounds described in the prior art, benzopyrans and naphthopyrans may be cited which are described in patents or patent applications U.S. Pat. Nos. 3,567,605, 3,627,690, 4,826,977, 5,200,116, 5,238,981, 5,411,679, 5,429,744, 5,451,344, 5,458,814, 5,651,923, 5,645,767, 5,698,141, 5,783,116, WO-A-95 05382, FR-A-2,718,447, WO-A-96 14596, and WO-A-97 21698, which are of the reduced formulae below:

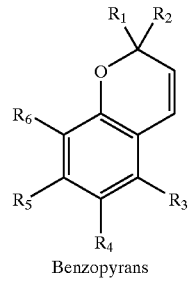

Benzopyrans

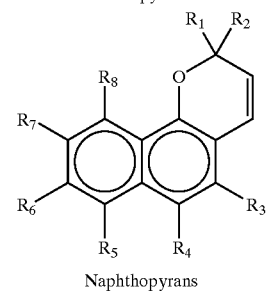

Naphthopyrans

Certain patents (e.g. EP-A-562 915, FR-A-2,718,447, U.S. Pat. No. 5,604,280, WO-A-95 05382, U.S. Pat. Nos. 5,429,774 and 5,411,679) relate more specifically to benzopyrans which are annelated with aromatic heterocycles. US patent U.S. Pat. No. 5,411,679 notably claims the general structure below:

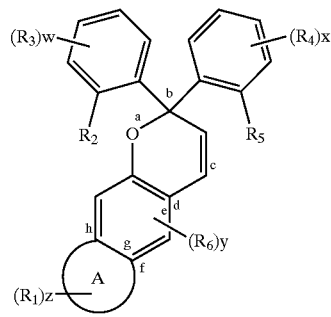

US-A-5,411,679 in which ring A is a substituted or non-substituted benzothieno- or benzofurano-type heterocycle, annelated in position 2,3 or 3,2 with sides f, g or h. In the case of the compounds in which A is fused on side h, y and z are equal to zero in the examples described and the discoloration kinetics are slow.

These compounds claim to satisfy the specifications defined above. In reality, if these compounds really do have one or more of the basic properties sought after, such as a high transmission in the absence of ultraviolets and a high colourability under solar irradiation, none of the compounds described hitherto have the complete combination of the properties sought after which are necessary for the production of satisfactory articles. In particular, none of these compounds is intrinsically grey or brown and the necessity of using an additional photochrome in order to obtain one of these two tints does subsist.

In this context, it is to the credit of the inventors for having been interested in this type of derivative as a base for developing novel photochromes, and for having proposed a novel family of molecules which have particularly advantageous photochromic properties.

Thus, according to a first of its aspects, the present invention relates to compounds of formula (I):

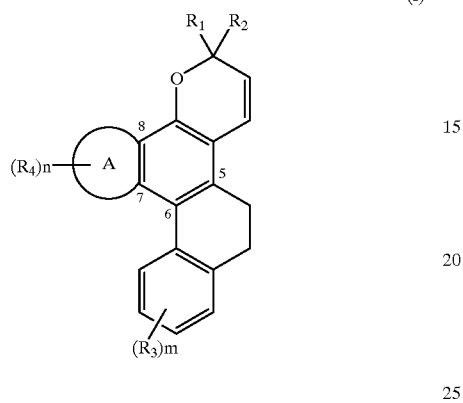

in which:

A is an aromatic heterocycle of the thieno, benzothieno, furano, benzofurano, pyrrolo, indolo, naphthofurano or naphthothieno type, said heterocycle being fused with the benzopyran in positions 2,3 or 3,2;

$R_1$ and $R_2$, which are identical or different, represent, independently:

hydrogen, a linear or branched alkyl group comprising 1 to 12 carbon atoms, a cycloalkyl group comprising 3 to 12 carbon atoms, an aryl or heteroaryl group comprising in its basic structure 6 to 24 carbon atoms or 4 to 24 carbon atoms respectively and at least one heteroatom selected from sulphur, oxygen and nitrogen; said basic structure being optionally substituted with at least one substituent selected from the whole of the substituents given below:

a halogen, and notably fluorine, chlorine and bromine, a hydroxy, a linear or branched alkyl group comprising 1 to 12 carbon atoms, a linear or branched alkoxy group comprising 1 to 12 carbon atoms, a haloalkyl or haloalkoxy group corresponding to the ($C_1$–$C_{12}$) alkyl or alkoxy groups above respectively which are substituted with at least one halogen atom, and notably a fluoroalkyl group of this type, a linear or branched alkenyl group comprising 2 to 12 carbon atoms, and notably a vinyl group or an allyl group, an —$NH_2$ group, an —NHR group, R representing a linear or branched alkyl group comprising 1 to 6 carbon atoms, a

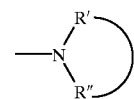

group, R' and R", which are identical or different, representing independently a linear or branched alkyl group comprising 1 to 6 carbon atoms or representing together with the nitrogen atom to which they are bound a 5- to 7-membered ring which can comprise at least one other heteroatom selected from oxygen, sulphur and nitrogen, said nitrogen being optionally substituted with an R'" group, which is a linear or branched alkyl group comprising 1 to 6 carbon atoms, a methacryloyl group or an acryloyl group, an aralkyl or heteroaralkyl group, the alkyl group, which is linear or branched, comprising 1 to 4 carbon atoms and the aryl part of which has the same definition as that given supra for the aryl and heteroaryl group;

or said two substituents $R_1$ and $R_2$ together form an adamantyl, norbornyl, fluorenylidene, di($C_1$–$C_6$) alkylanthracenylidene or spiro($C_5$–$C_6$) cycloalkylanthracenylidene group; said group being optionally substituted with at least one of the substituents listed above for $R_1$, $R_2$: an aryl or heteroaryl group;

$R_3$ and $R_4$, which are identical or different, represent, independently:

a halogen, and notably fluorine, chlorine or bromine, a hydroxy, a linear or branched alkyl group comprising 1 to 12 carbon atoms (advantageously 1 to 6 carbon atoms), a cycloalkyl group comprising 3 to 12 carbon atoms, a linear or branched alkoxy group comprising 1 to 12 carbon atoms (advantageously 1 to 6 carbon atoms), a haloalkyl, halocycloalkyl, or haloalkoxy group corresponding to the alkyl, cycloalkyl, alkoxy groups above respectively, which are substituted with at least one halogen atom, notably selected from fluorine, chlorine and bromine, an aryl or heteroaryl group having the same definition as that given supra for $R_1$, $R_2$, an aralkyl or heteroaralkyl group, the alkyl group, which is linear or branched, comprising 1 to 4 carbon atoms, and the aryl and heteroaryl groups having the same definitions as those given supra for $R_1$, $R_2$, an amine or amide group: —$NH_2$, —NHR, —$CONH_2$, —CONHR,

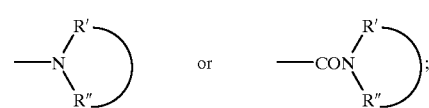

R, R', R" having their respective definitions given supra for the amine substituents of the values $R_1$, $R_2$: aryl or heteroaryl, an —$OCOR_6$ or —$COOR_6$ group, $R_6$ representing a straight or branched alkyl group comprising 1 to 6 carbon atoms, or a cycloalkyl group comprising 3 to 6 carbon atom's, or a phenyl group, optionally substituted with at least one of the substituents listed above for the values of $R_1$, $R_2$: aryl or heteroaryl;

or
at least two of the $R_3$ groups, which are adjacent, form a 5- to 6-membered aromatic or non-aromatic ring which can comprise at least one heteroatom selected from the group comprising oxygen, sulphur or nitrogen and/or at least one substituent selected from a $C_1-C_6$ alkyl group which is linear or branched, a $C_1-C_6$ alkoxy group which is linear or branched, and an amine group of formula $—NH_2$, $—NHR$ or

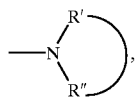

as defined above, as substituent, of the basic structure of the aryl or heteroaryl group representing $R_1$ or $R_2$; and m and n are integers of 0 to 4.

The person skilled in the art will obviously have understood that the branched alkyl, alkoxy and alkenyl groups, as defined above, comprise a sufficient number of carbon in order to be branched (i.e. more than 3, more than 3, and more than 4 carbon atoms respectively).

The compounds of the invention—annelated benzopyrans of formula (I)—have very fast discoloration kinetics.

Amongst said compounds of the invention, preferred are those which have the formula (I) in which:

$R_1$, $R_2$ are identical or different and represent independently optionally substituted aryl or heteroaryl groups the basic structure of which is selected from the group comprising phenyl, naphthyl, biphenyl, pyridyl, furyl, benzofuryl, dibenzofuryl, N—($C_1-C_6$)alkylcarbazole, thienyl, benzothienyl, dibenzothienyl and julolidinyl groups ; $R_1$ and/or $R_2$ representing, advantageously, a para-substituted phenyl group;

or $R_1$ and $R_2$ together form an adamantyl or norbornyl group;

$R_3$ represents a halogen, an alkyl group or an alkoxy group ; and n=0 and m=1.

According to a second of its aspects, the present invention relates to a method of preparation of the compounds (I), characterised in that it consists essentially of carrying out a condensation:

of an intermediate product of formula (II) given below:

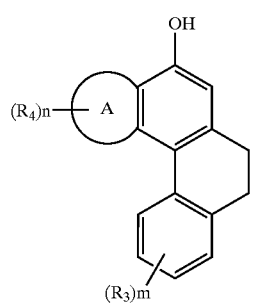

in which A, $R_3$, $R_4$, m and n are as defined above with reference to formula (I), with a derivative of propargylic alcohol, having formula (III) below:

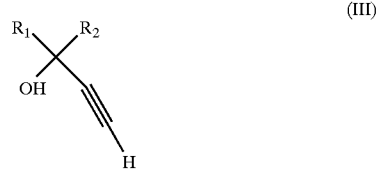

in which $R_1$ and $R_2$ are as defined supra with reference to formula (I);

the condensation (II)/(III) being carried out advantageously in the presence of a catalyst, this catalyst being preferably selected from the group comprising para-toluenesulphonic acid, dodecylsulphonic acid or bromoacetic acid;

or with an aldehyde derivative, having formula (III') below:

in which $R_1$ and $R_2$ are as defined supra with reference to formula (I);

the condensation (II/(III') being carried out, advantageously, in the presence of a metallic complex, preferably a complex of titanium, titanium (IV) ethoxide being particularly preferred.

In practice, the condensation reaction between compounds (II) and (III') can take place in solvents such as toluene, xylene or tetrahydrofuran, to which appropriate catalysts are optionally added. For more details on the condensation of compounds (II), (III'), reference may be made to the EP-A-0 562 915 patent application.

The compounds of formula (III) are known to the person skilled in the art and are obtained from the corresponding ketone according to a method described notably in the WO-A-96 14596 patent application. The ketone is itself commercial or is prepared according to the known methods such as the Friedel Crafts method (cf. WO-A-96 14596 and cited references).

Aldehydes (III'), which are derivatives of (III), are obtained by rearrangement in an acid medium (cf. J. Org. Chem., 1977, 42, 3403).

The compounds of formula (IIa) and (IIb) (compounds of formula (II) in which the heterocycle is annelated in 2,3 or 3,2 respectively) are obtained according to a synthetic scheme the various steps of which are adaptations of known methods. The preferred general synthesis scheme is given below:

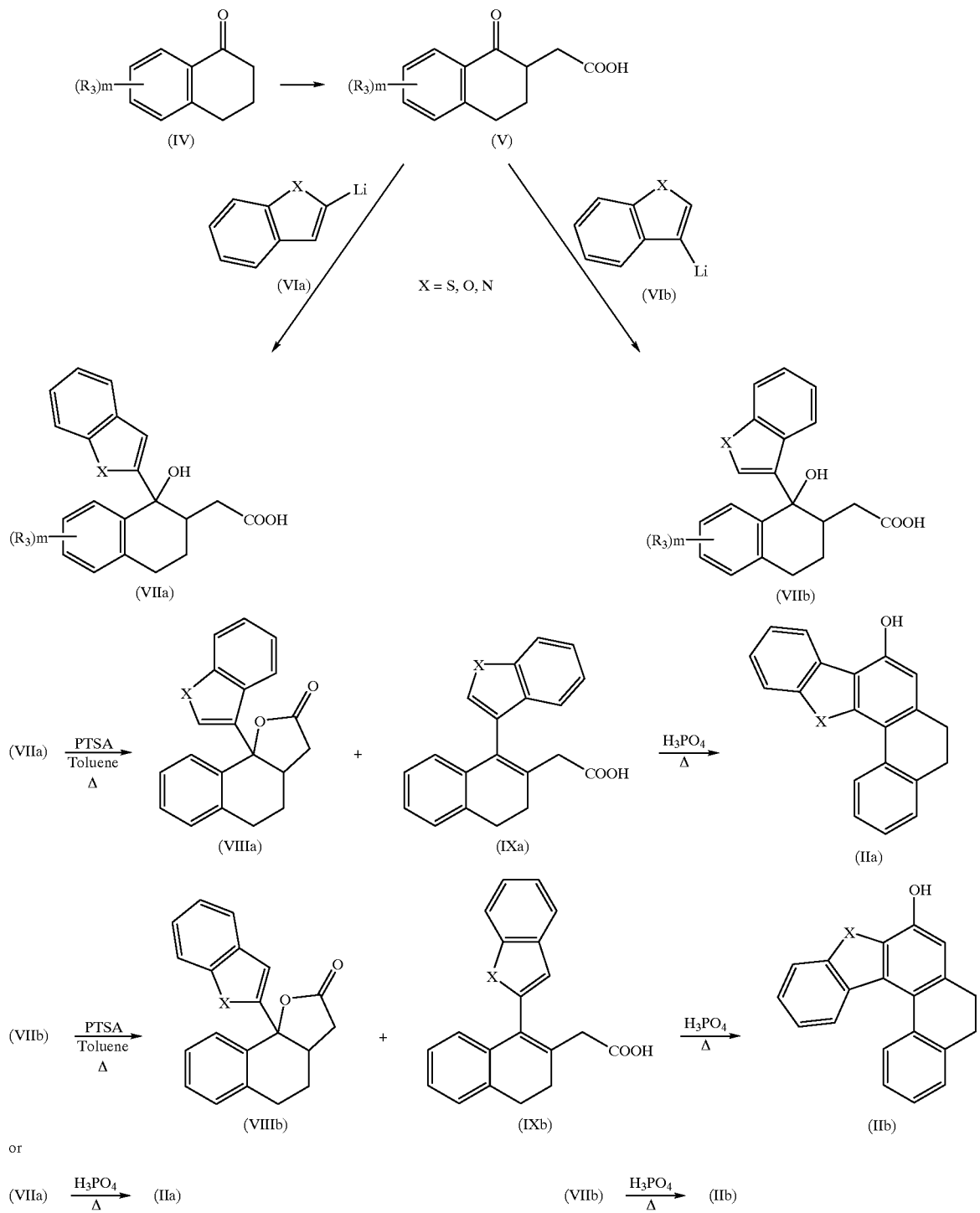

In a first sequence, tetralone (IV) is converted into tetralone (V) according to known methods (cf. WO 96/38435 and U.S. Pat. No. 3,980,699).

The action of two equivalents of organolithium (VIa) (cf. *The Chemistry of Heterocycles,* Stuttgart; New York: Thieme, 1995) or (VIb) (cf. *J. Chem. Soc.* (C) 1971, 3447–3454) leads to compounds (VIIa) and (VIIb) respectively which are dehydrated to give mixtures (VIIIa)+(IXa) and (VIIIb)+(IXb) respectively. These compounds are then cyclised to give (IIa) and (IIb) respectively in phosphoric acid. The cyclisation giving (IIa) and (IIb) in phosphoric acid can also be carried out on compounds (VIIa) and (VIIb).

According to a third of its aspects, the invention also relates to the novel intermediate products of formula (II) recalled below:

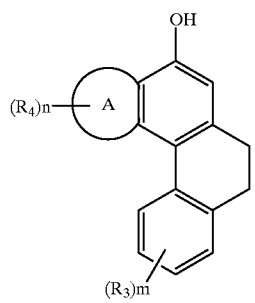

(II)

in which A, $R_3$, $R_4$, m and n are as defined supra with reference to formula (I).

According to a fourth of its aspects, the object of the invention is (co)polymer(s) and/or reticulate(s) obtained by polymerising and/or cross-linking and/or grafting at least one monomer consisting of a compound (1) as defined above. Thus, the compounds (I) according to the invention can be per se (co)monomers and/or be comprised in (co) polymerisable and/or cross-linkable (co)monomers. The (co)polymers and/or reticulates thus obtained can constitute photochromic matrices such as those presented infra.

According to a fifth of its aspects, the present invention relates to the use of said compounds of formula (I) of the invention as photochromic agents. Another object of the invention is, therefore:

firstly, novel photochromic compounds which are constituted by the $C_7$–$C_8$-annelated benzopyran derivatives such as defined above, taken alone or in a mixture of themselves and/or with at least one other photochromic compound of another type and/or with at least one non-photochromic colouring agent;

secondly, novel photochromic compositions which comprise at least one compound (I) as defined above, and/or at least one linear or cross-linked (co)polymer containing at least one compound (I) according to the invention in its structure. Such photochromic compositions can contain at least one other photochromic compound, of another type and/or at least one non-photochromic colouring agent and/or at least one stabilising agent. These photochromic compounds of another type, non-photochromic colouring agents, and stabilising agents are prior art products known to the person skilled in the art.

Within the context of the present invention, combinations of photochromic compounds of the invention and/or combinations of photochromic compounds of the invention and photochromic compounds of another type according to the prior art are particularly recommended; such combinations being interesting in that they are suitable for generating grey or brown tints, which are desired by the public in applications such as ophthalmic spectacles or solar spectacles. These additional photochromic compounds can be those known to the person skilled in the art and described in the literature, e.g. chromenes (U.S. Pat. Nos. 3,567,605, 5,238, 981, WO-A-94 22850, EP-A-0 562 915), spiropyrans or naphthospiropyrans (U.S. Pat. No. 5,238,981) and spiroxazines (Crano et al., "Applied Photochromic Polymer Systems", Ed. Blackie & Son Ltd, 1992, chapter 2).

Said compositions according to the invention can also comprise:

non-photochromic colouring agents which enable adjusting the tint, and/or one or more stabilising agents, such as an anti-oxidising agent for example, and/or one or more anti-UV, and/or one or more anti-radicals, and/or one or more photochimic excited state deactivators.

These additives can notably enable improving the durability of said compositions.

The compounds of the invention envisaged within the context of their photochromic applications can be used in solution. Thus, a photochromic solution can be obtained by dissolving at least one of said compounds in an organic solvent such as toluene, dichloromethane, tetrahydrofuran or ethanol. The solutions obtained are in general colourless and transparent. When exposed to sunlight, they develop a strong coloration and regain the colourless state when they are placed in an area of less exposure to the sun's rays or, in other words, when they are no longer submitted to UV. In general, a very low concentration of product (of the order of 0.01 to 5% by weight) is sufficient to obtain an intense coloration.

The compounds according to the invention are furthermore compatible with support matrices of organic polymer or of inorganic material (even of an inorganic-organic hybrid material), in a form included in said matrices as well as in the form of a coating of said matrices.

Also, within the context of the fifth aspect of the invention in relation to the photochromic applications, the object of the invention is a matrix which comprises:

at least one compound (I), as defined supra;

and/or at least one (co)polymer and/or reticulate, as defined supra;

and/or at least one composition, as presented above.

The most interesting applications of the compounds of the invention are in fact those in which the photochrome is dispersed uniformly within or on the surface of a matrix formed by a polymer and/or copolymer and/or mixture of (co)polymers.

Following the example of their behaviour in solution, the compounds (I), included in a polymer matrix are colourless or slightly coloured in the initial state and rapidly develop an intense coloration under a UV light (365 nm) or under a light source of the solar type. Finally, they regain their initial coloration once the irradiation ceases.

The methods of implementation which can be envisaged in order to obtain such a matrix are very varied. Amongst those known to the person skilled in the art, the diffusion in the (co)polymer, from a suspension or solution of the photochrome, in a silicone oil, in an aliphatic or aromatic hydrocarbon, or in a glycol, or from another polymer matrix, can be cited for example. The diffusion is commonly carried out at a temperature of 50 to 200° C. for a period of time of 15 minutes to several hours, according to the nature of the polymer matrix. Another implementation technique consists in mixing the photochrome in a formulation of polymerisable materials, depositing this mixture on a surface or in a mould, and then carrying out the copolymerisation. These implementation techniques, and others, are described in the article by Crano et al. "Spiroxazines and their use in photochromic lenses" published in Applied Photochromic Polymer Systems, Ed. Blackie and Son Ltd -1992.

The following products may be mentioned as examples of preferred polymer materials for forming matrices which are useful in optical applications of the photochromic compounds according to the invention:

alkyl, cycloalkyl, (poly or oligo)ethylene glycol, aryl or arylalkyl poly(mono-, di- tri- or tetra)acrylate or poly(mono-, di-, tri- or tetra)methacrylate, which is optionally halogenated or which comprises at least one ether and/or ester and/or carbonate and/or carbamate and/or thiocarbamate and/or urea and/or amide group, polystyrene, polyether, polyester, polycarbonate (e.g. bisphenol-A polycarbonate, diallyl diethylene glycol polycarbonate), polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate or polyvinylbutyral, those obtained from difunctional monomers having the formula below:

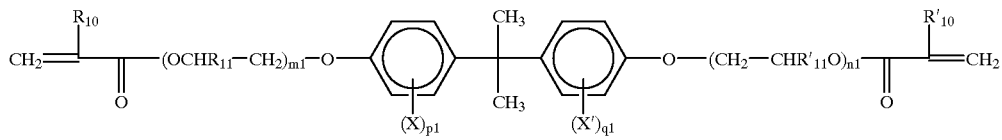

in which:

$R_{10}$, $R'_{10}$, $R_{11}$ and $R'_{11}$ are identical or different and represent independently a hydrogen or a methyl group;

$m_1$ and $n_1$ are, independently, integers between 0 and 4 (inclusive) ; and are advantageously independently equal to 1 or 2;

X and X', which are identical or different, are a halogen and represent, preferably, a chlorine and/or a bromine;

$p_1$ and $q_1$ are, independently, integers between 0 and 4 (inclusive);

copolymers of at least two types of copolymerisable monomers selected from the precursor monomers of the polymers listed supra, and preferably those belonging to the groups comprising: (meth)acrylic monomers, vinylic monomers, allylic monomers, and mixtures thereof In a particularly preferred manner, the photochromes of the invention are used with resins which have a nanobiphasic structure and which are obtained by copolymerising at least two different, specific difunctional monomers. Such resins have been described by the Applicant in the French patent Application FR-A-2,762,845 and International patent Application WO-A-98 504 43.

The amount of photochrome used in the (co)polymer matrix depends upon the degree of darkening desired. Usually, between 0.001 and 20% by weight of it is used.

Still according to the fifth of its aspects in relation to the applications of the compounds (I) as photochromes, another object of the present invention is ophthalmic articles, such as ophthalmic or solar spectacle articles, comprising:

at least one compound (I) according to the invention, and/or at least one (co)polymer and/or reticulate formed, at least in part, from compound(s) of the invention, and/or at least one photochromic composition as defined above, and/or at least one matrix (as defined supra), of an organic polymer material or of an inorganic material, or even of a hybrid inorganic-organic material, said matrix initially comprising at least one compound of the invention.

In practice, the articles which are more particularly covered by the present invention are ophthalmic lenses or photochromic solar lenses, glazing (windows for buildings, for locomotion engines, automobile vehicles), optical devices, decorative articles, solar protection articles, information storage, . . .

The present invention is illustrated by the Examples which follow of synthesis and of photochromic validation, of compounds of the invention.

EXAMPLES

Example 1

Synthesis of Compound (1)

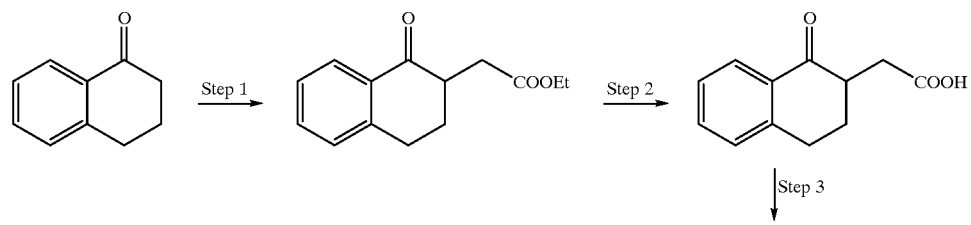

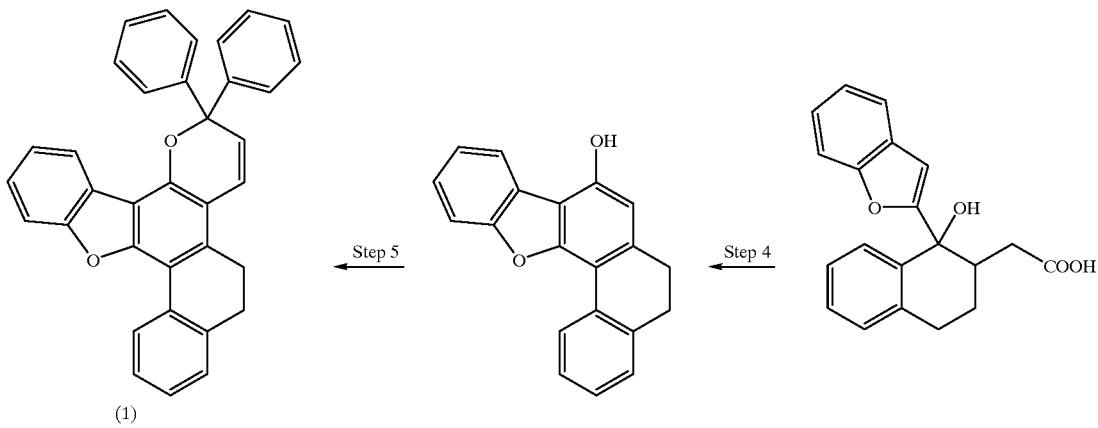

Step 1
120 ml of a 2M solution of LDA are added at −70° C. to a solution of 29.24 g of α-tetralone in 150 ml of anhydrous THF. Stirring is effected for 30 min at −70° C., and 26.6 ml of ethyl bromoacetate in solution in 25 ml of anhydrous THF are then added. The temperature is allowed to rise and stirring is effected at 0° C. for 1 hour 30 minutes. 10 ml of ethyl bromoacetate are added and stirring is effected for 1 hour at 0° C. The reaction mixture is poured into 300 ml of 1N hydrochloric acid to which ice ad been added. Extraction is carried out with ethyl acetate, the organic phase is dried over magnesium sulphate and the solvents are evaporated off. The resulting red oil (about 40 g) is used as such for the next step.

Step 2
A solution of potassium hydroxide (40 g) in ethanol (500 ml) is added to the product of step 1 and stirring is effected under reflux for 45 min. The ethanol is evaporated off, water is added, and washing is carried out with diisopropyl ether. The aqueous phase is concentrated, and then acidifed to pH=1. After extraction with ethyl acetate, drying over magnesium sulphate and evaporation of the solvent, about 38 g of a red oil are obtained which is purified by chromatography on a silica column (elution heptane/EtOAc 8/2 and then gradient to 6/4) in order to give, after recrystallisation from an EtOAc/diisopropyl ether mixture, 16.4 g of white crystals.

Step 3
25 ml of a 1.6M solution de n-butyllithium are added at −78° C. to a solution of 3.93 g of benzofuran in 30 ml of anhydrous THF. Stirring is effected for 15 minutes at −78° C., and then for 15 minutes at 0° C. This solution is added to a solution of 3.06 g of the product of step 2 in 20 ml of anhydrous THF, and stirring is effected for 1 hour at 0° C. The reaction mixture is poured into an iced 1N solution of HCl, extracted with ethyl acetate, and dried over magnesium sulphate. The solvent is evaporated off. The resulting yellow oil is dissolved in diisopropyl ether and extracted with 1N sodium hydroxide. The aqueous phase is acidified, and extracted with ethyl acetate. After drying over magnesium sulphate and evaporation of the solvent, about 4 g of an orange oil are obtained which is used as such for the next step.

Step 4
The product of the preceding step is dissolved in 40 ml of toluene. 15 ml of a aqueous solution (85%) of phosphoric acid are added, and stirring is effected under reflux (heating>150° C.). The solvents are collected with a Dean-Stark, and stirring at about 150–200° C. for 45 minutes is then effected. After cooling, the reaction mixture is poured into water and extracted with ethyl acetate. After drying over magnesium sulphate and evaporation of the solvents, a dark oil is obtained which is partially purified over silica (elution: heptane/EtOAc 8/2). The resulting red oil (about 1.9 g) is extracted with a 2N solution of KOH and then acidifed and extracted with ethyl acetate. After drying over magnesium sulphate and evaporation of the solvent, 900 mg of a brown meringue are obtained.

Step 5
A few PTSA crystals are added to a solution of 900 mg of the product of step 4 and 641 mg of 1,1-diphenylpropyn-1-ol in 20 ml of xylene. The mixture is stirred under reflux for 30 minutes, cooled, and purified by filtration over silica (elution: toluene/heptane 1/1). The resulting yellow solid is recrystallised from a toluene/ethanol mixture in order to give 920 mg of just yellow crystals which is pure by $^1$H NMR.

Example 2
Synthesis of Compound (2)
Its synthesis was carried out according to a method analogous to that used for compound (1). The two first steps are identical.

Step 3
34.4 ml of a 1.6M solution of n-butyllithium are added at −78° C. to a solution of 7.38 g of thianaphthene in 20 ml of anhydrous THF. After addition, stirring is effected for 1 hour 30 minutes at about −10° C., are the mixture obtained is then added to a solution of 5.11 g of the product of step 2 in 20 ml of anhydrous THF. Stirring is effected for 1 hour at −50° C., and the mixture is poured into a 1N solution of HCl. The mixture is extracted with ethyl acetate, dried over magnesium sulphate, and the solvent is evaporated off. The resulting pink oil (about 13 g) is dissolved in an EtOAc/diisopropyl ether mixture and extracted with 1N sodium hydroxide. The aqueous phase is acidified with HCl, and extracted with ethyl acetate. After drying over magnesium sulphate and evaporation of the solvent, an orange oil (7.2 g) is obtained which is used as such for the next step.

Step 4
The product of step 3 is dissolved in 50 ml of toluene and 30 ml of an aqueous solution (85%) of phosphoric acid is added. Stirring is effected under reflux (heating>150° C.), and the solvents are distilled off with the aid of a Dean-Stark apparatus. The mixture is stirred at about 150–200° C. for 30 min, and is then cooled. Water is added, and the brown precipitate formed is then filtered off. The latter is dissolved in 100 ml of ethyl acetate, and is washed with 50 ml of a 0.2N solution of sodium hydroxide. The organic phase is dried over magnesium sulphate and is evaporated and then filtered over silica (elution: heptane/EtOAc 7/3) and the brown solid obtained is recrystallised from diisopropyl ether in order to give 1.18 g of a beige solid.

Step 5

The method is identical to that described for Example 1. 305 mg of just yellow crystals (which are recrystallised from ethyl acetate and which are in accordance with the expected structure ($^1$H NMR)) are obtained from 302 mg of the product of step 4 and 204 mg of 1,1-diphenylpropyn-1-ol.

Example 3
Synthesis of Compound (3)

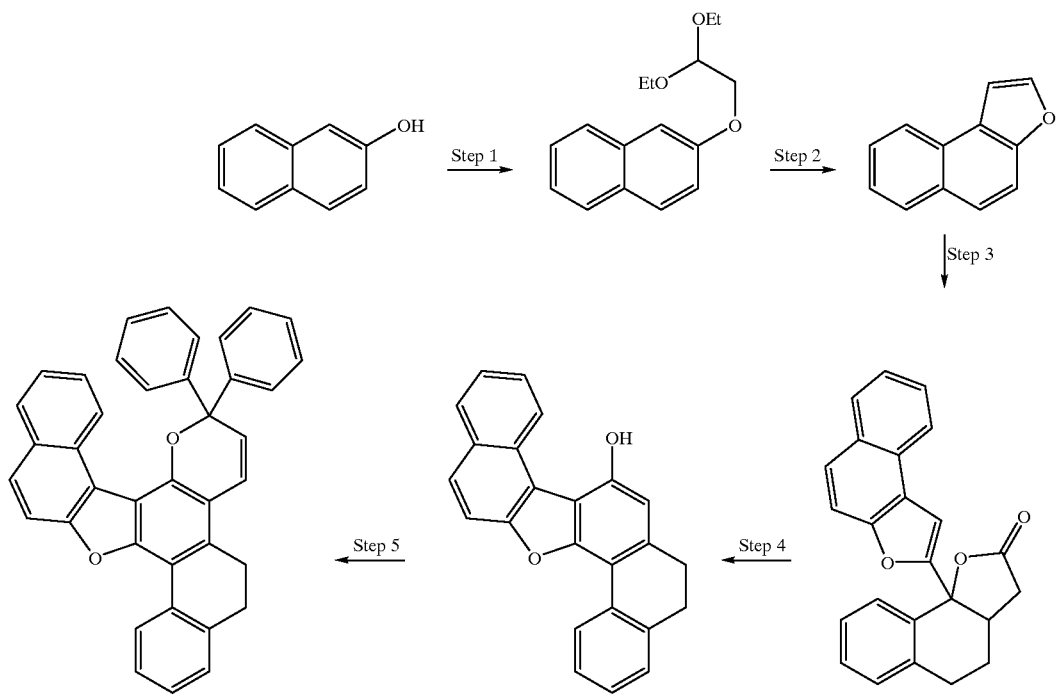

Step 1

A solution of 14.4 g of 2-naphthol in 50 ml of THF is added at 0° C. to a suspension of 4.4 g of NaH (60%, dispersion in mineral oil) in 25 ml of THF. The temperature is allowed to rise to room temperature, 25 ml of THF are added and stirring is effected for 30 min. 16.55 ml of pure BrCH$_2$CH(OEt)$_2$ are added, and then 50 ml of toluene. The THF is distilled off with the aid of a Dean-Stark apparatus, and 25 ml of DMF are then added. After 2 hours of reflux, 1 g of NaH and 6 ml of BrCH$_2$CH(OEt)$_2$ are added successively. Stirring is effected under reflux for 1 hour more, before the mixture is poured into 200 ml of 0.5N HCl. After extraction with diisopropyl ether, drying over magnesium sulphate and evaporation of the solvent, a red oil is obtained which is purified by chromatography on a silica column (elution: toluene/heptane 1/1) in order to give 26.05 g of a just yellow oil.

Step 2

3.74 g of the product of step 1 are dissolved in 50 ml of toluene and 10 ml of an aqueous solution (85%) of phosphoric acid are then added. Stirring is effected under reflux for 30 minutes, and the water-toluene azeotrope is then distilled off with the aid of a Dean-Stark apparatus. After 1 hour 30 minutes, the mixture is cooled and water is added. The reaction mixture is extracted with ethyl acetate. The organic phase was dried over magnesium sulphate and the solvent is evaporated off with caution (the product sublimes easily). The resulting beige solid (2.5 g) is used as such for the next step.

Step 3

13.75 ml of a 1.6M solution of n-butyllithium are added at −78° C. to a solution of 3.69 g of the product of step 2 in 20 ml of anhydrous THF. Stirring is effected for 30 minutes, and the mixture obtained is added at 0° C. to a solution of 2.04 g of the product of step 2 of the compound (1) in 10 ml of anhydrous ether. Stirring is effected for 1 hour 30 minutes at 0° C., and the mixture is poured into 25 ml of an iced solution of 1N HCl. The mixture is extracted with ethyl acetate, dried over magnesium sulphate and the solvents are evaporated off. The residue is dissolved in 100 ml of toluene, a few PTSA crystals are added and stirring is effected under reflux for 1 hour. After evaporation of the solvent, the resulting dark oil is purified by chromatography on a silica column (elution: heptane/EtOAc 8/2) in order to give 800 mg of a grey solid.

Step 4

The product of step 3 is dissolved in 30 ml of toluene, 10 ml of an aqueous solution (85%) of phosphoric acid are then added, and stirring is effected under reflux. The solvents are distilled off with the aid of a Dean-Stark apparatus, and stirring is effected at about 150–200° C. for 1 hour 30 minutes. The mixture is cooled, water is added and is extracted with ethyl acetate. After drying over magnesium sulphate and evaporation of the solvents, the resulting dark oil is purified by chromatography on a silica column (elution: heptane/EtOAc 8/2, and then gradient to 6/4) in order to give 250 mg of a beige solid.

Step 5

A few PTSA crystals were added to a solution of 250 mg of the product of step 4 and 270 mg of 1,1-diphenylpropyn- 1-ol in 10 ml of xylene. The mixture is stirred under reflux for 1 hour, cooled, and purified by filtration over silica (elution: toluene/heptane 1/1). The resulting yellow solid is recrystallised from a diisopropyl ether/heptane mixture in order to give 250 mg of just yellow crystals which is pure by $^1$H NMR.

Example 4

The photochromic properties of said compounds (1), (2) and (3) were evaluated. To this end, said compounds are incorporated, at the rate of about 0.05% by weight, in a matrix. A mixture of the starting materials is in fact made, the nature and the incorporated amounts of which materials are specified below; this mixture is poured into a lens mould of 2 mm thickness and which is then subjected to a heating cycle of 2 hours at 70° C. and then of 1 hour at 100° C. Precursor starting materials of the matrix:

0.05 parts by weight of the photochromic colouring agent: compound (1), (2) or (3); per 60 parts by weight of DIACRYL 121 from AKZO Chimie (tetraethoxylated bisphenol A dimethacrylate);

10 parts by weight of divinylbenzene;

30 parts by weight of polyethylene glycol dimethacrylate from ALDRICH;

0.5 parts by weight of n-dodecanethiol;

0.2 parts by weight of AMBN (2,2'-azobis(2-methylbutyronitrile) provided by AKZO (Perkadox®)).

Said matrix, which contains said photochromic compounds within its mass, is exposed to UV rays (source: xenon lamp). The $\lambda_{max}$'s in the visible and the discoloration kinetics are given in the Table below. Said discoloration kinetics are measured by the decrease in the absorbance at the λmax of the activated form after irradiation (T1/2=time for the absorbance to decrease by a half). The properties of these compounds are given in the Table below.

| COMPOUND | STRUCTURE | λ1* | λ2** | $T_{1/2}$ |
|---|---|---|---|---|
| (1) | 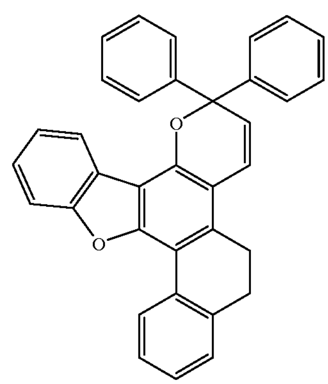 | 424 nm | 579 nm | 15 s |
| (2) | 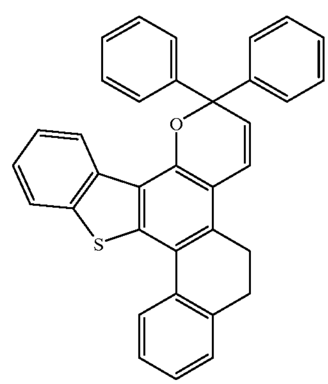 | 445 nm | 584 nm | 16 s |

-continued

| COMPOUND | STRUCTURE | λ1* | λ2** | $T_{1/2}$ |
|---|---|---|---|---|
| (3) | 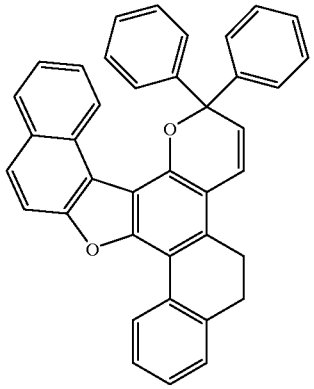 | 431 nm | 589 nm | 19 s |

*λ1 max of the band of the shortest wavelength in the visible spectrum of the compound after exposure.
**λ2 max of the band of the longest wavelength of the compound after exposure.

The observation of the matrices in the presence of solar or UV rays shows that the compounds of the invention have very rapid discoloration kinetics and that they possess λ2's which are shifted towards longer wavelengths (bathochromic shift). Moreover, the absorption band situated in λ1 is more intense than that situated in λ2.

What is claimed is:

1. A compound of the following formula (I):

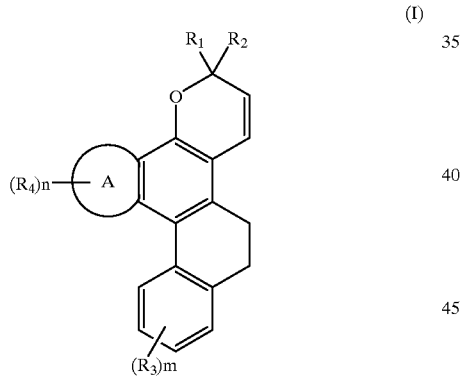

(I)

in which:

A is an aromatic heterocycle of the thieno, benzothieno, furano, benzofurano, pyrrolo, indolo, naphthofurano, or naphthothieno type, said heterocycle being fused with the benzopyran in positions 2,3 or 3,2;

$R_1$ and $R_2$, which are identical or different, represent, independently:
hydrogen,
a linear or branched alkyl group comprising 1 to 12 carbon atoms,
a cycloalkyl group comprising 3 to 12 carbon atoms,
an aryl group comprising, in its basic structure, 6 to 24 carbon atoms or a heteroaryl group comprising, in its basic structure, 4 to 24 carbon atoms and at least one heteroatom selected from sulphur, oxygen, and nitrogen; said basic structure being optionally substituted with at least one substituent selected from the group consisting of:

a halogen,
a hydroxy group,
a linear or branched alkyl group comprising 1 to 12 carbon atoms,
a linear or branched alkoxy group comprising 1 to 12 carbon atoms,
a haloalkyl or haloalkoxy group corresponding to the ($C_1$-$C_{12}$) alkyl or alkoxy groups above, respectively, which are substituted with at least one halogen atom,
a linear of branched alkenyl group comprising 2 to 12 carbon atoms,
an —$NH_2$ group,
an —NHR group, wherein R represents a linear or branched alkyl group comprising 1 to 6 carbon atoms,
a

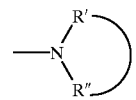

group, wherein R' and R", which are identical or different, represent, independently, a linear or branched alkyl group comprising 1 to 6 carbon atoms or R' and R", together with the nitrogen atom to which they are bound, represent a 5- to 7-membered ring which optionally comprises at least one other heteroatom selected from oxygen, sulphur, and nitrogen, said nitrogen being optionally substituted with an R''' group, which is a linear or branched alkyl group comprising 1 to 6 carbon atoms, and a methacryloyl group or an acryloyl group, or an aralkyl or heteroaralkyl group, the alkyl part of which is linear or branched and comprises 1 to 4 carbon atoms and the aryl or heteroaryl part of which has the same definition as that given above for the aryl and heteroaryl group;

or said two substituents $R_1$ and $R_2$ together form an adamantyl, norbornyl, fluorenylidene, di($C_1$-$C_6$)

alkylanthracenylidene, or spiro($C_5$-$C_6$) cycloalkylanthracenylidene group; said group being optionally substituted with at least one substituent selected from the group consisting of:
a halogen,
a hydroxy group,
a linear or branched alkyl group comprising 1 to 12 carbon atoms,
a linear or branched alkoxy group comprising 1 to 12 carbon atoms,
a haloalkyl or haloalkoxy group corresponding to the ($C_1$-$C_{12}$) alkyl or alkoxy groups above, respectively, which are substituted with at least one halogen atom,
a linear or branched alkenyl group comprising 2 to 12 carbon atoms,
an —$NH_2$ group,
an —NHR group, wherein R represents a linear or branched alkyl group comprising 1 to 6 carbon atoms,
a

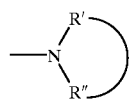

group, wherein R' and R", which are identical or different, represent, independently, a linear or branched alkyl group comprising 1 to 6 carbon atoms or R' and R", together with the nitrogen atom to which they are bound, represent a 5- to 7-membered ring which optionally comprises at least one other heteroatom selected from oxygen, sulphur, and nitrogen, said nitrogen being optionally substituted with an R''' group, which is a linear or branched alkyl group comprising 1 to 6 carbon atoms, and
a methacryloyl group or an acryloyl group;
$R_3$ and $R_4$, which are identical or different, represent, independently:
a halogen,
a hydroxy group,
a linear or branched alkyl group comprising 1 to 12 carbon atoms,
a cycloalkyl group comprising 3 to 12 carbon atoms,
a linear or branched alkoxy group comprising 1 to 12 carbon atoms,
a haloalkyl, halocycloalkyl, or haloalkoxy group corresponding to the alkyl, cycloalkyl and alkoxy groups above, respectively, which are substituted with at least one halogen atom,
an aryl or heteroaryl group having the same definition as that given above for $R_1$, $R_2$,
an aralkyl or heteroaralkyl group, the alkyl part of which is linear or branched and comprises 1 to 4 carbon atoms and the aryl or heteroaryl part of which has the same definition as that given above for $R_1$, $R_2$,
an amine or amide group: —$NH_2$, —NHR, —$CONH_2$, —CONHR,

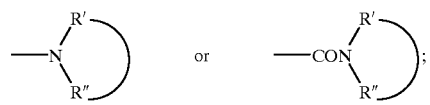

wherein R represents a linear or branched alkyl group comprising 1 to 6 carbon atoms and wherein R' and R", which are identical or different, represent, independently, a linear or branched alkyl group comprising 1 to 6 carbon atoms or R' and R", together with the nitrogen atom to which they are bound, represent a 5- to 7-membered ring which optionally comprises at least one other heteroatom selected from oxygen, sulphur, and nitrogen, said nitrogen being optionally substituted with an R''' group, which is a linear or branched alkyl group comprising 1 to 6 carbon atoms, or
an —$OCOR_6$, —$COOR_6$, wherein $R_6$ represents a straight or branched alkyl group comprising 1 to 6 carbon atoms, or a cycloalkyl group comprising 3 to 6 carbon atoms, or a phenyl group, optionally substituted with at least one substituent selected from the group consisting of:
a halogen
a hydroxy group,
a linear or branched alkyl group comprising 1 to 12 carbon atoms,
a linear or branched alkoxy group comprising 1 to 12 carbon atoms,
a haloalkyl or haloalkoxy group corresponding to the ($C_1$-$C_{12}$) alkyl or alkoxy groups above, respectively, which are substituted with at least one halogen atom,
a linear or branched alkenyl group comprising 2 to 12 carbon atoms,
an —$NH_2$ group,
an —NHR group, wherein R represents a linear or branched alkyl group comprising 1 to 6 carbon atoms,
a

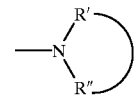

group, wherein R' and R", which are identical or different, represent, independently, a linear or branched alkyl group comprising 1 to 6 carbon atoms or R' and R", together with the nitrogen atom to which they are bound, represent a 5- to 7-membered ring which optionally comprises at least one other heteroatom selected from oxygen, sulphur, and nitrogen, said nitrogen being optionally substituted with an R''' group, which is a linear or branched alkyl group comprising 1 to 6 carbon atoms, and
a methacryloyl group or an acryloyl group
or
at least two of the $R_3$ groups which are adjacent form a 5- to 6-membered aromatic or non-aromatic ring which can optionally comprise at least one heteroatom selected from the group consisting of oxygen, sulphur, and nitrogen and which can optionally comprise at least one substituent selected from a $C_1$-$C_6$ linear or branched alkyl group, a $C_1$–$C_6$ linear or branched alkoxy group, and an amine group of formula —$NH_2$, —NHR or,

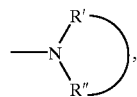

as defined above; and m and n are integers of 0 to 4.

2. A compound according to claim 1, wherein:

$R_1$ and $R_2$ are identical or different and represent, independently, optionally substituted aryl or heteroaryl groups, the basic structure of which is selected from phenyl, naphthyl, biphenyl, pyridyl, furyl, benzofuryl, dibenzofuryl, N-($C_1$–$C_6$)alkylcarbazole, thienyl, benzothienyl, dibenzothienyl, and julolidinyl groups; or $R_1$ and $R_2$ together form an adamantyl or norbornyl group;

$R_3$ represents a halogen, an alkyl group, or an alkoxy group; and n=0 and m=1.

3. A method of preparing a compound according claim 1, said method comprising:

condensing an intermediate compound of the following formula (II):

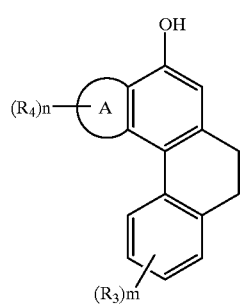

in which in which A, $R_3$, $R_4$, m, and n are as defined in claim 1 with a propargylic alcohol derivative having the following formula (III):

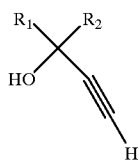

in which $R_1$ and $R_2$ are as defined in claim 1, wherein said condensing of (II)/(III) is optionally carried out in the presence of a catalyst; or with an aldehyde derivative having formula (III') below:

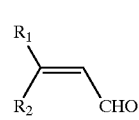

in which $R_1$ and $R_2$ are as defined in claim 1, wherein said condensing (II)/(III') is optionally carried out in the presence of a metallic complex.

4. A (co)polymer and/or reticulate obtained by polymerising and/or cross-linking and/or grafting at least one monomer comprising a compound according to claim 1.

5. A photochromic material, wherein said photochromic material is constituted by:

a compound according to claim 1, a mixture at least two compounds according to claim 1, or a mixture of at least one compound according to claim 1 with at least one other photochromic compound of another type and/or at least one non-photochromic colouring agent.

6. A photochromic composition comprising:

at least one compound according to claim 1, and/or at least one linear or cross-linked (co)polymer which contains, in its structure, at least one compound according to claim 1, and optionally, at least one other photochromic compound of another type and/or at least one non-photochromic colouring agent and/or at least one stabilising agent.

7. A (co)polymer matrix comprising at least one compound according to claim 1.

8. A (co)polymer matrix comprising at least one composition according to claim 6.

9. A (co)polymer matrix comprising at least one co(polymer) and/or reticulate according to claim 4.

10. A (co)polymer matrix according to claim 7 further comprising one or more (co)polymer selected from the group consisting of:

an alkyl, cycloalkyl, (poly or oligo)ethylene glycol or aryl or arylalkyl mono-, di-, tri-, or tetraacrylate or mono-, di-, tri-, or tetramethacrylate which is optionally halogenated or which optionally comprises at least one ether and/or ester and/or carbonate and/or carbamate and/or thiocarbamate and/or urea and/or amide group;

polystyrene, polyether, polyester, polycarbonate, polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate, or polyvinylbutyral;

(co)polymers obtained from difunctional monomers having the formula below:

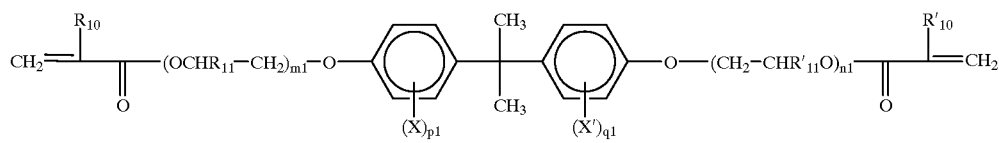

in which $R_{10}$, $R'_{10}$, $R_{11}$, and $R'_{11}$ are identical or different and represent, independently, a hydrogen or a methyl group;

$m_1$ and $n_1$ are, independently, integers between 0 and 4, inclusive;

X and X', which are identical or different, are a halogen;

$p_1$ and $q_1$ are, independently, integers between 0 and 4, inclusive; and copolymers of at least two types of copolymerisable monomers selected from the precursor monomers of the polymers listed above.

11. An ophthalmic or solar article comprising at least one compound according to claim 1.

12. An ophthalmic or solar article according to claim 11 comprising a lens, a glazing, an optical device, or a combination thereof.

13. An ophthalmic or solar article comprising at least one composition according to claim 6.

14. An ophthalmic or solar article according to claim 13 comprising a lens, a glazing, an optical device, or a combination thereof.

15. An ophthalmic or solar article comprising at least one (co)polymer and/or reticulate according to claim 4.

16. An ophthalmic or solar article according to claim 15 comprising a lens, a glazing, an optical device, or a combination thereof.

17. An ophthalmic or solar article comprising at least one (co)polymer matrix according to claim 7.

18. An ophthalmic or solar article according to claim 17 comprising a lens, a glazing, an optical device, or a combination thereof.

* * * * *